United States Patent
Anumula

[11] Patent Number: 5,968,834
[45] Date of Patent: *Oct. 19, 1999

[54] METHOD OF CARBOXY TERMINAL PROTEIN OR PEPTIDE SEQUENCING

[75] Inventor: Kalyan Rao Anumula, King of Prussia, Pa.

[73] Assignee: SmithKline Beecham Corporation, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/767,122

[22] Filed: Dec. 9, 1996

Related U.S. Application Data

[62] Division of application No. 08/427,029, Apr. 24, 1995, Pat. No. 5,641,685.

[51] Int. Cl.[6] .................................................. G01N 33/68
[52] U.S. Cl. ............................... 436/89; 436/90; 530/345
[58] Field of Search ............................... 436/89, 90, 161, 436/172; 530/345, 402, 427

[56] References Cited

U.S. PATENT DOCUMENTS

| | | | |
|---|---|---|---|
| 4,837,165 | 6/1989 | Hawke | 436/89 |
| 5,180,807 | 1/1993 | Bailey et al. | 436/89 |
| 5,185,266 | 2/1993 | Boyd et al. | 436/89 |

OTHER PUBLICATIONS

Inglis, Adam S., Chemical Procedures for C–Terminal Sequencing of Peptides and Proteins, Analytical Biochemistry 195, pp. 183–196 (1991).

Stark, George R., Sequential Degradation of Peptides from Their Carboxyl Terinini with Ammonium Thiocyanate and Acetic Anhydride, Biochemistry, vol. 7, No. 5, May 1968, pp. 1796–1807 (1968).

*Primary Examiner*—Lyle A. Alexander
*Attorney, Agent, or Firm*—Dara L. Dinner; Stephen Venetianer; Charles M. Kinzig

[57] ABSTRACT

The present invention provides for an efficient and novel method for the C-terminal sequencing of proteins or peptides by use of acetyl chloride or phosphoryl chloride by reaction with a suitable isothiocyanate for derivitation of the carboxy terminus to a thiohydantoin amino acid derivative, under acidic conditions. Cleavage of the derivatized thiohydantoin amino acid may occur by use of thiocyanic acid and acetic acid in water and also by the novel means using a buffer and a potassium or sodium thiocyanate or potassium or sodium dithionite reagent. The present invention also provides for an novel and efficient means for the C-terminal sequencing of proteins or peptides by a two or three step process which comprises first reacting the peptide or protein with an acid chloride reagent, such as acetyl chloride, or phosphoryl chloride. The stable protein carboxy terminal amino acid chloride is then reacted with an organic isothiocyanate, an organic salt thiocyanate, or a metal thiocyanate to yield a thiohydantoin amino acid derivative. This thiohydantoin amino acid derivative may be cleaved using either acidic or basic condition, preferably using the novel reagents disclosed above.

19 Claims, 11 Drawing Sheets

METHOD OF CARBOXY TERMINAL PROTEIN OR PEPTIDE SEQUENCING

This is a divisional of application Ser. No. 08/427,029, filed Apr. 24, 1995, now U.S. Pat. No. 5,641,685.

FIELD OF THE INVENTION

The present invention relates to a method, and reagents useful therein for determining the C-terminal amino acid of a peptide or protein and the process of sequencing the peptide or protein from the C-terminal end thereof.

BACKGROUND OF THE INVENTION

The sequencing of proteins from the carboxyl terminus has been a challenging problem in protein structure determination. Many methods for N-terminal sequencing have been published and readily available to the skilled artisan but little has been accomplished relative to the C-terminus, and fewer methods have resulted in commercial usage.

The thiocyanate method, described by Schlack et al., Physiol. Chem., 154:125;14 170 (1926) involved the reaction of a protein or peptide with certain isothiocyanate reagents, in the presence of acetic anhydride, to form a C-terminal thiohydantoin amino acid. The derivatized amino acid is hydrolyzed to yield a shortened polypeptide and a thiohydantoin amino acid. The thiohydantoin amino acids are now analyzed by HPLC methods. A disadvantage of this reaction is the severity of the conditions required for complete derivatization of the C-terminal amino acid.

Stark, G. R., Biochemistry, 7:1796–1807 (1968) introduced use of the reagent acetohydroxamate as one more mild and capable of performing a more rapid cleavage. U.S. Pat. No. 4,837,165 discloses the use of the reagent trimethylsilylisothiocyanate (TMS-ITC) which resulted in an improved yield of the thiohydantoin formation and reduced the number of side products obtained. The yields were low upon repetition which limited the number of degradation cycles to be performed. Further, not all amino acids were able to form thiohydantoin derivatives by this method.

Bailey et al., U.S. Pat. No. 5,180,807; discloses the use as a sequencing agent of an isothiocyanate regent which is a combination of phophoroisothiocyanatidate and pyridine. The phophoroisothiocyanatidate includes a diphenyl moiety of the formula $(Ph))_2$-P(O)-NCS or a diethyl derivative $(EtO)_2$-P(O)-NCS. Bailey et al, U.S. Pat. No. 5,227,309 discloses using an alkyl or aryl tin isothiocyanate derivative, such as $R_xSn(NCS)_y$. Bailey et al., U.S. Pat. No. 5,254,475 discloses use of alkali metal salts of trialkyl silanols and trialkylamine N-oxides, utilized in preference with silyl isothiocyanate as the coupling reagent.

Boyd et al., U.S. Pat No. 5,185,266 discloses a method for cleaving the acyl thiohydantoin bond with an alkylating agent to form an adduct on the thiohydantoin. The adduct containing acyl-thiohydantoin is cleaved by reaction under substantially anhydrous acidic conditions.

Boyd et al., U.S. Pat. No. 5,051,368 discloses a method for forming thiohydantoins by activation of the amino acid with a ketenimine, and converting the ester to a thiohydantoin by reaction with a silyl or pyridine isothiocyanate.

Boyd et al., U.S. Pat. No. 5,041,388 discloses use of a mixed anhydride of isothiocyanic acid and a carboxylic or carbonic acid, for use under basic condition which reacts the peptide with the activated support derivatized as noted.

Boyd et al., U.S. Pat. No. 5,304,497 discloses a method of forming an N-protected amino acid for use in C-terminal peptide sequencing which utilizes uronium compounds with preferred thiocyanate such as TMS-ITC, or crown ether adducts of metallothiocyanates.

Miller, U.S. Pat. No. 4,935,494 discloses phophoryl (thio) amide coupling reagents to yield arylthiohydantoin derivatives of amino acids. Miller et al., U.S. Pat. No. 5,066,785 discloses a coupling reagent for use in C-terminal peptides of the formula $(R_1)_nX_a$-P(=$X_c$)(($R_2)_nX_b$)-N($R_3$)-(C=$X_d$)-$X_e$.

Patent Applications to Hawke et al., U.S. Pat. No. 5,049,507 discloses a method of C-terminal sequencing wherein the peptide is reacted with a mixed anhydride of isothiocyanic acid and carboxylic, carbonic or sulfonic acid under basic conditions.

Various substrate materials for use in sequencing C-terminal peptides have been proposed by Bailey et al., in U.S. Pat. No. 5,306,781 which discloses an activated carboxylic acid modified polyethylene membrane and in Sherrington et al., in U.S. Pat. No. 5,066,784 which discloses a pourous polymeric material.

SUMMARY OF THE INVENTION

The present invention is to the preparation of thiohydantoin amino acids (TH-AAs) at the C-terminal of proteins by use of the reagent acetylisothiocyanate (Ac-NCS) under acidic conditions in a one step process suitable for manual sequencing. The thiocyanate mediated cleavage (acidic or basic) of the TH-AAs from proteins constitutes a novel chemistry for C-terminal sequencing of proteins and is comparable to the known Edman degradation of proteins and peptides.

Another embodiment of the present invention is the preparation of thiohydantoin amino acids (TH-AAs) at the C-terminal of proteins by use of an acid chloride, preferably the reagent acetyl chloride, or to create an protein carboxy chloride derivative which is then reacted with a suitable isothiocyanate to form the thiohydantoin amino acid (TH-AAs) which may be cleaved under acidic or basic conditions. This two step reaction process is appropriately suited to use in a commercial setting, such as in an automated sequencing machine.

DETAILED DESCRIPTION OF THE INVENTION

There are many problems in carboxy-terminal sequencing which include chemistry of C-terminal derivatization; cleavage of the C-terminal derivatives; identification of the derivatives; availability of proper amino acid standards; and the yield of thiohydantoins at each step. The instant invention provides for readily accessible chemistry to yield a derivatized thiohydantoin derivative. The thiohydantoin derivative is readily cleavable, in good yield, to allow identification of the resultant amino acid using known techniques and standards.

One aspect of the present invention is the discovery of a C-terminal derivatization process which yields thiohydantoin amino acids (TH-AAs) through use of acetylchloride (Ac-Cl) and a suitable thiocynate/isothiocyanate to yield the reagent acetyl isothiocyanate (Ac-NCS); or the use of phosphoryl chloride P(O)Cl$_3$ and a suitable thiocyanate/isothiocyanate to yield reagent (P(O)Cl$_2$-NCS (P(O)NCS) for manual sequencing. Preferably the final reagent used is Ac-NCS.

It is recognized that reaction of the P(O)Cl$_3$ moiety with an isothiocyanate will yield combinations of final reagents, of P(O)Cl(NCS)$_2$, P(O)Cl$_2$NCS or P(O)(NCS)$_3$ or combinations thereof. All are acceptable for use herein, their amounts determined by molar equivalents, as one skilled in the art would readily recognize.

One embodiment, therefore, of the present invention, is the preparation of thiohydantoin amino acids (TH-AAs) at the C-terminal of proteins by use of the reagents Ac-NCS, P(O)NCS, or P(Et)NCS, under acidic conditions, in a one step process, which process is suitable for manual sequencing. The thiocyanate mediated cleavage (acidic or basic) of the TH-AAs from proteins constitutes novel chemistry for C-terminal sequencing of proteins and is comparable to the known Edman degradation of proteins and peptides.

An advantage of this invention is that the acetyl isothiocyanate can be readily prepared in short time, approximately 10 minutes, and the thiohydantoin standards are also easily prepared from free amino acids.

Figure 1:
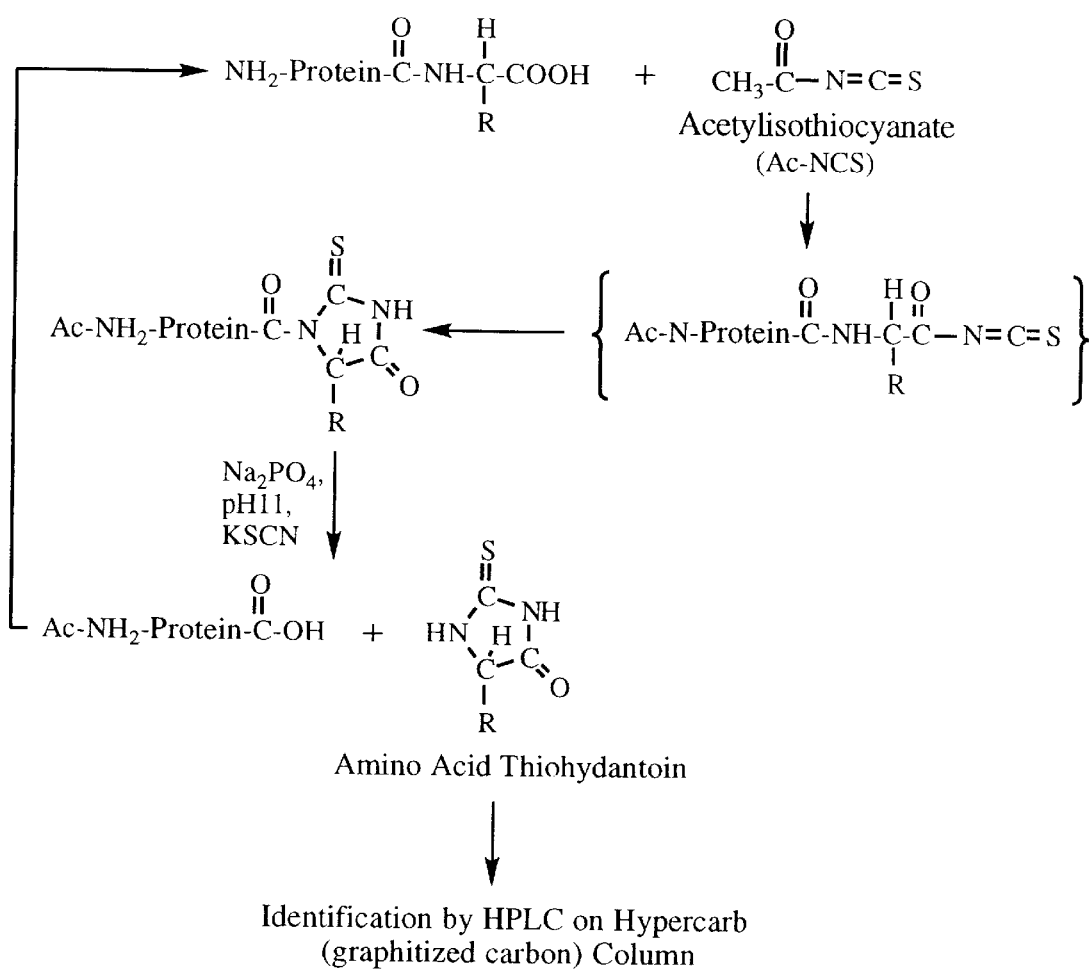
FIG. 1 demonstrates a proposed reaction scheme for the sequencing and determination of a C-terminal amino acids by reaction of a suitable protein or peptide with the reagent acetylisothiocyanate to form a carboxy-terminal thiohydantoin derivative. The carboxy-terminal thiohydantoin derivative is cleaved in this instance, under basic reaction conditions using a phosphate buffer, and potassium thiocyanate to release the thiohydantoin amino acid derivative which is then analyzed by HPLC.
Figure 2:
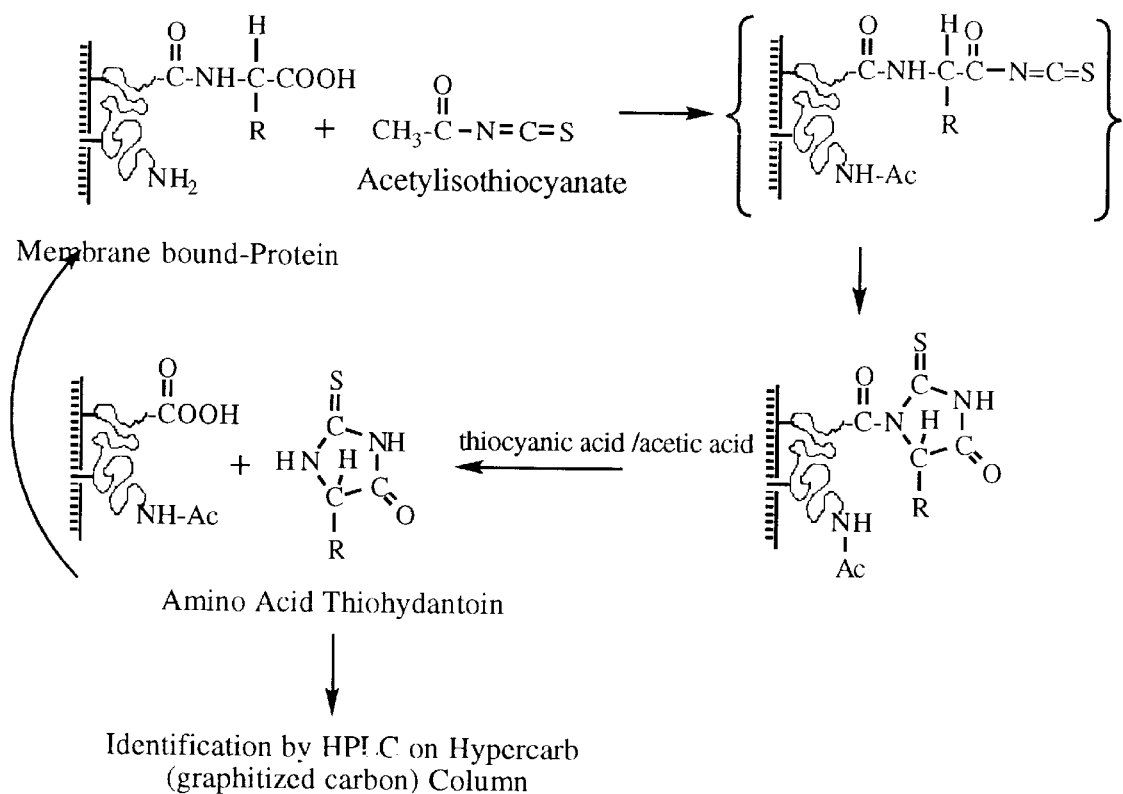
FIG. 2 demonstrates a proposed reaction scheme for the sequencing and determination of a C-terminal amino acids by reaction of an immobilized suitable protein or peptide with the reagent acetylisothiocyanate to form a carboxy-terminal thiohydantoin derivative. The carboxy-terminal thiohydantoin derivative is cleaved in this instance, using thiocyanic acid and acetic acid.
Figure 3:
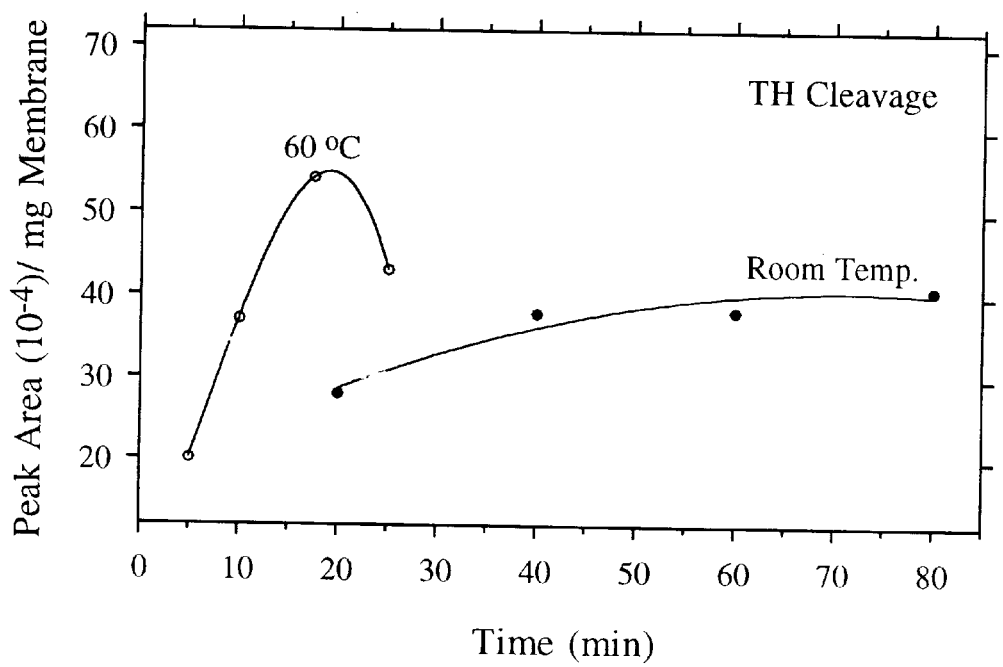
FIG. 3 demonstrates a graph which shows the stability of the C-terminal thiohydantoin amino acids over a pH range. At elevated temperatures or under increasing pH the thiohydantoin derivative is not stable and cleaves from the carboxy end of the protein or peptide.
Figure 4:
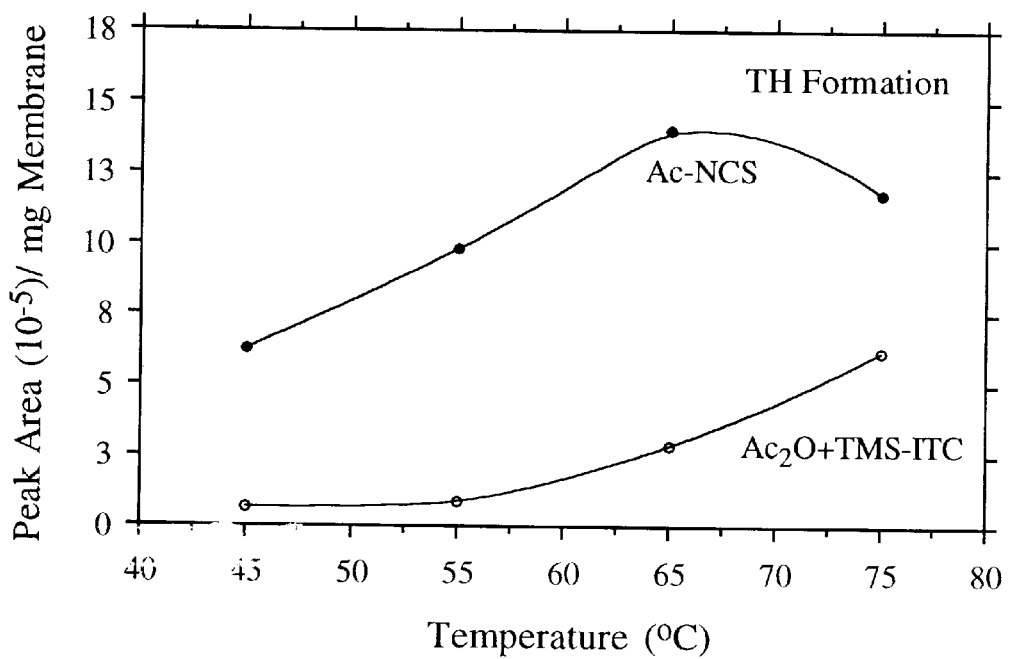
FIG. 4 demonstrates a temperature dependency, as analyzed by HPLC, on the formation of the thiohydantoin amino acid derivative of the carboxy terminus.
Figure 5:
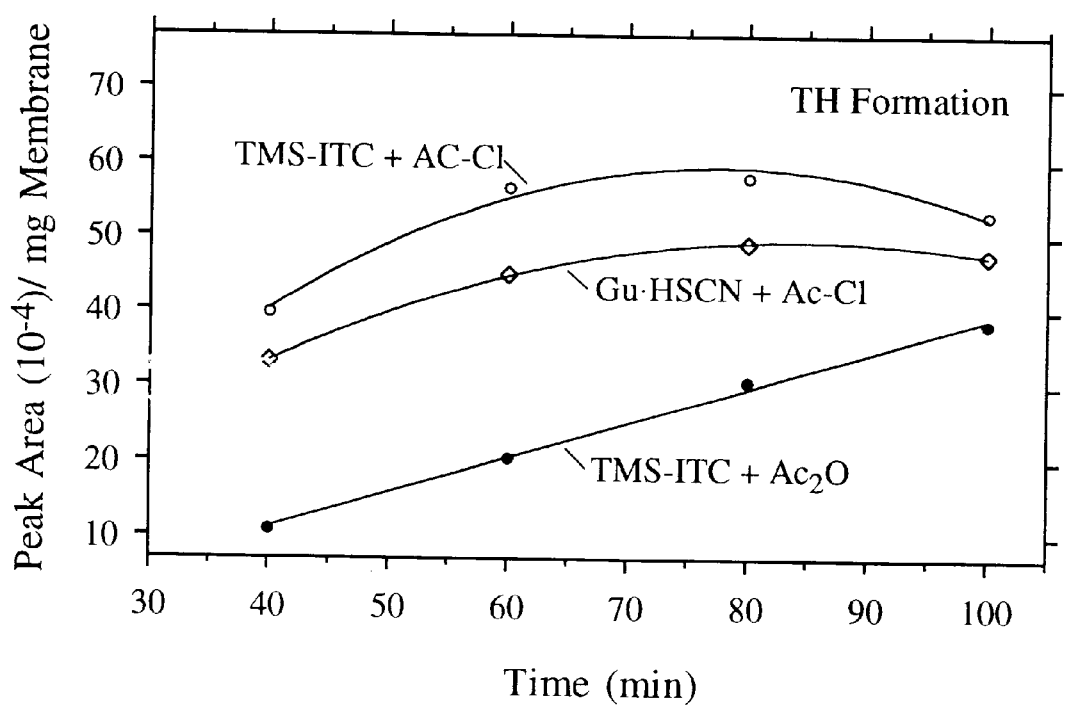
FIG. 5 demonstrates a time dependency, as analyzed by HPLC, on the formation of the thiohydantoin amino acid derivative of the carboxy terminus.
Figure 6:
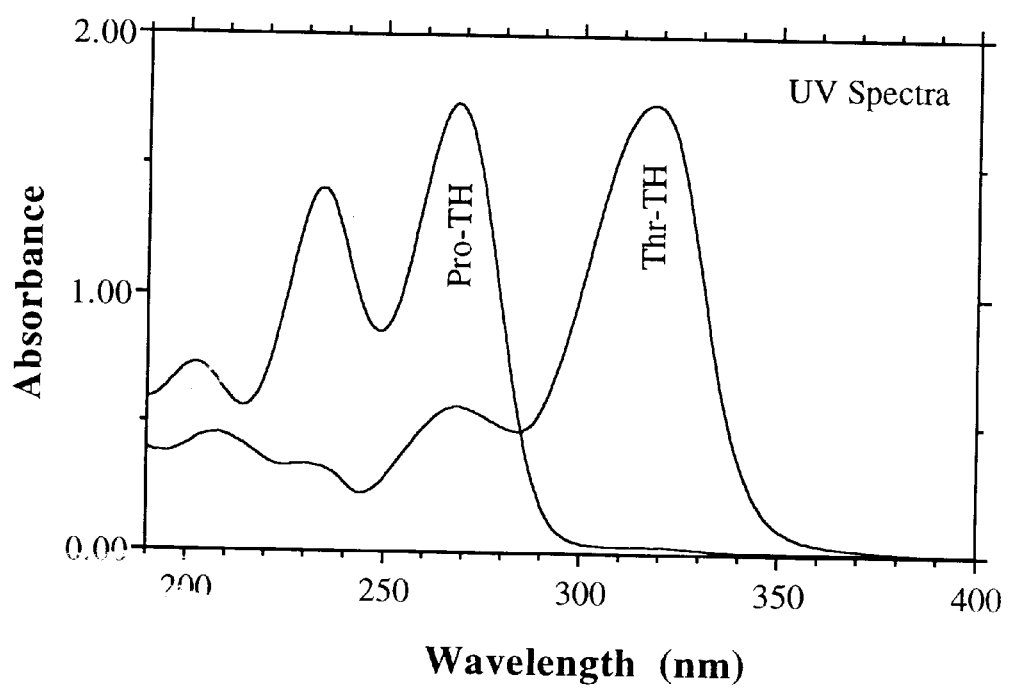
FIG. 6 demonstrates an absorption spectra of the thiohydantoin amino acid derivatives of proline and threonine prepared in mg amounts.

Another aspect of the present invention is the novel cleavage of the TH-AA's from the peptide, or free amino acids for use in making standards. As described herein, cleavage of the C-terminal derivatized TH-AAs from the protein may be carried out under either acidic or basic conditions. A preferred embodiment of the present invention is the use of the novel reagent, a mixture a thiocyanate, preferably an alkali metal or alkaline earth metal thiocyanate, more preferably sodium or potassium thiocyanate, or an alkali metal or alkaline earth metal di-thionite (S$_2$O$_4$), preferably potassium or sodium dithionite (S$_2$O$_4$), and buffer, such as a Na phosphate buffer, carbonate buffer or a borate buffer, preferably a Na phosphate buffer, in an organic solvent. Suitably, the molar concentration of each is about 0.01M to 0.2M, preferably about 0.1M. Suitably the organic solvent is acetonitrile, short chain alcohol, such as methanol, isopropanol, ethanol, t-butanol, n-butanol, preferably acetonitrile, from about 0.5–20% (v/v). The pH is suitably from about 8 to 12, suitably from 10 to 12. The reaction can take place at ambient temperature, or preferably at increased temperatures, such as from about 40 to 60° C. The reaction should also take from about 5 minutes to several hours, preferably from about 10 to 20 minutes at 60° C. A comparison of room temperature versus elevated temperatures for a thiocyanate mediated basic cleavage of the TH-AA from the protein is further described in FIG. 3.

Figure 7:
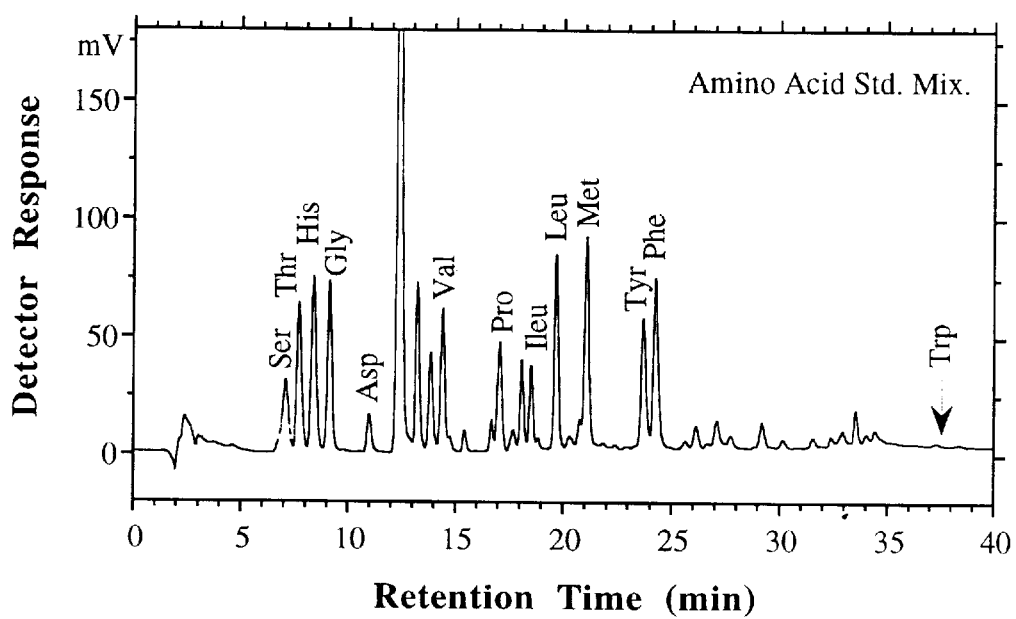
FIG. 7 demonstrates an analysis of a mixture of amino acid thiohydantoin standards as analyzed by HPLC. The large peak present in the amino acids is presumably due to the acetyl-SCN formed along with the acetyl-NCS and is easily removed by the treatment, for instance, with base.
Figure 8:
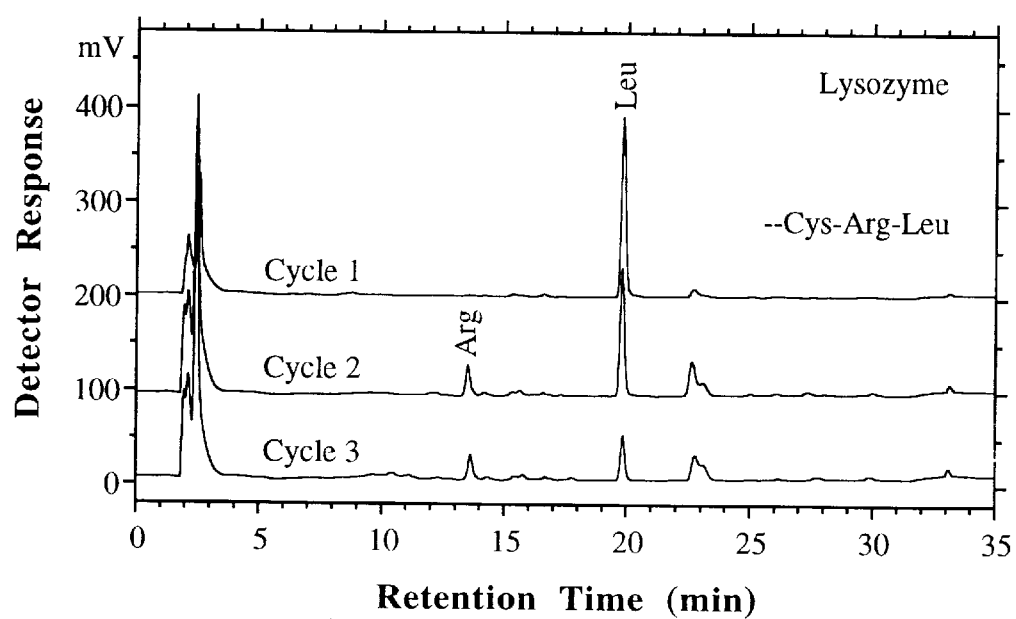
FIG. 8 demonstrates the C-terminal sequencing of the protein lysozyme by HPLC analysis for three cycles.
Figure 9:
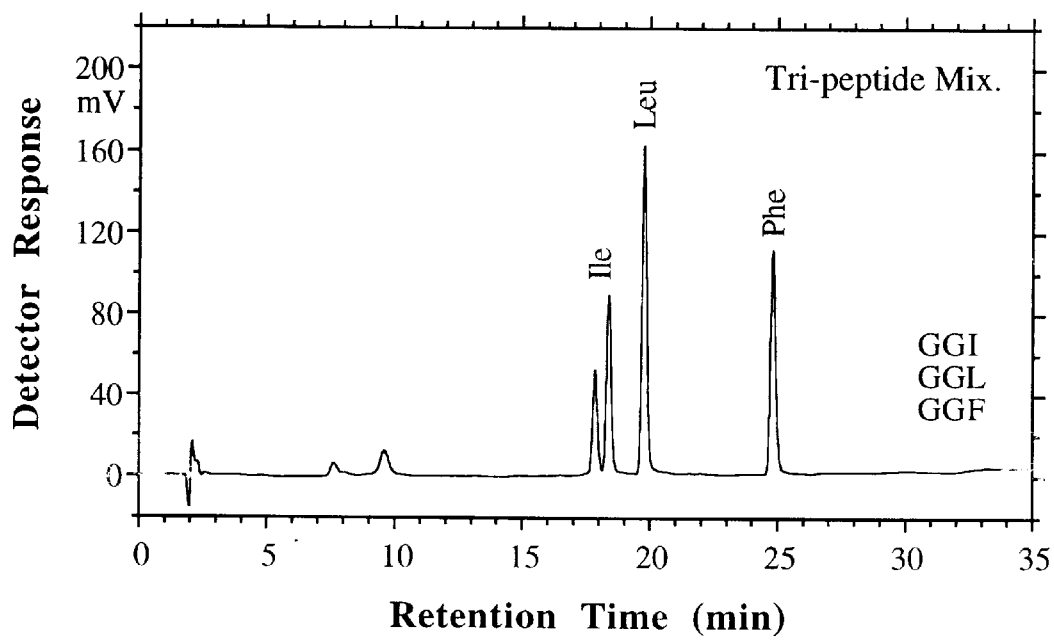
FIG. 9 demonstrates the C-terminal sequencing of a mixture of three peptides, GGI, GGL, GGF by HPLC analysis for one cycle.

Another aspect of the present invention is the novel cleavage of the TH-AA's from the protein under acidic conditions using a suitable acid, such as from about 0.1M to 1.5M thiocyanic acid with acetic acid. The reaction can take place at ambient temperature or at elevated temperatures. The reaction should also take from about 20 minutes to an hours, preferably from about 25 to 45 minutes. A demonstration of acidic cleavage is shown in FIG. 7 which is the final products of derivatization and cleavage of thiohydantoin amino acids. Free amino acids were appropriately derivatized with acetylisothiocyanate in solution, to which was added water creating a mixture of thiocyanic acid with acetic acid in equimolar proportions from use of the Ac-NCS as a reagent (for derivatization of the TH-AA).

Another aspect of the present invention is the preparation of thiohydantoin amino acids (TH-AAs) at the C-terminal of proteins by sue of an acid chloride, preferably the reagents acetyl chloride, CH$_3$S(O)$_2$Cl, P(O)Cl$_3$, diethyl phosphoryl chloride, or phenylene P(O)$_3$Cl, to create a protein carboxy chloride derivative which is then reacted with a suitable isothiocyanate to form the thiohydantoin amino acid (TH-AAs). This two step reaction process when added to a third, cleavage step under acidic or basic conditions, as described above, is appropriately suited for use in automated sequencing machines.

As uses herein, the peptide or protein moiety is also represented by the figure:

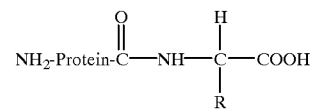

As use herein, the peptide carboxy chloride derivative is represented by the figure:

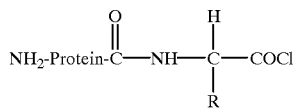

One Step Process

In the one step process the isothiocyanate coupling reagents may be prepared with a suitable isothiocyanate reagents, preferably either by reaction with KSCN or with trimethylsilyl isothiocyanate (TMS-ITC).

The C-terminal derivatization is then carried out under acidic conditions, using acetic acid, trifluoroacetic acid and hydrochloric acid, preferably acetic acid. The reaction may be done under temperature conditions of about 20 to about 80° C., preferably about 65° C. Suitably the time period for reaction is from about 5 minutes to about 80 minutes, preferably about 40 min.

Cleavage of the C-terminal TH-AAs from the protein may be carried out under either acidic or basic conditions as described above. It is recognized that use of the reagent Ac-NCS in this one step process will produce acidic conditions for cleavage of the TH-AA's from protein. Such conditions can be facilitated by treatment of the supported peptide with addition of water. The reaction can take place at ambient temperature or at any elevated temperature, such from about 40 to 80° C. The reaction should also take from about 20 minutes to an hours, preferably from about 25 to 45 minutes.

Two Step Process

Figure 10:
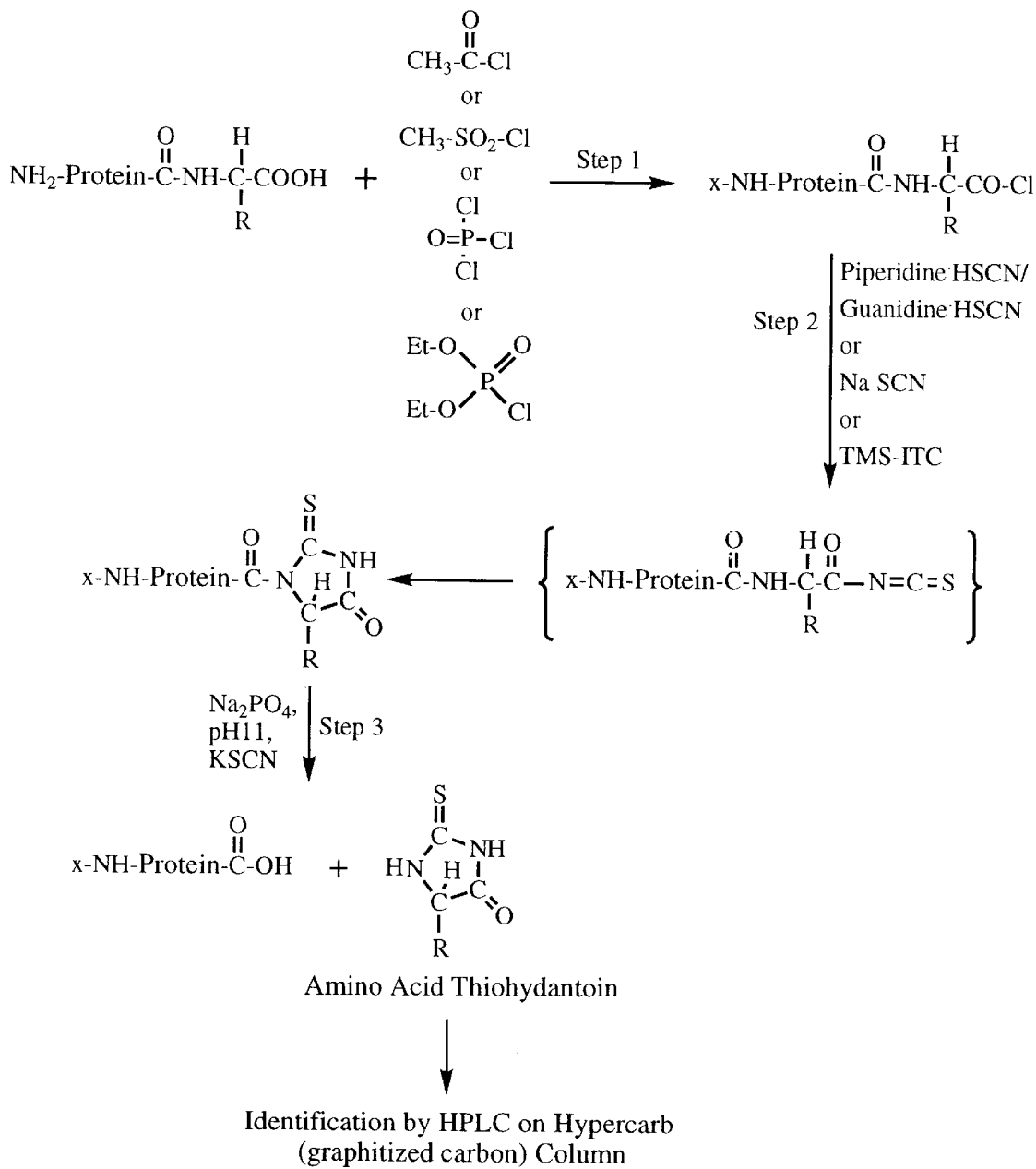
FIG. 10 demonstrates a proposed reaction scheme for the sequencing and determination of a C-terminal amino acids by reaction of an immobilized suitable protein or peptide with an acid chlorides and thiocyanate salts to form a carboxy terminal thiohydantoin derivative. The carboxy-terminal thiohydantoin derivative is cleaved in this instance, under basic reaction conditions using a phosphate buffer, and potassium thiocyanate to release the thiohydantoin amino acid derivative which is then analyzed by HPLC.
Figure 11:
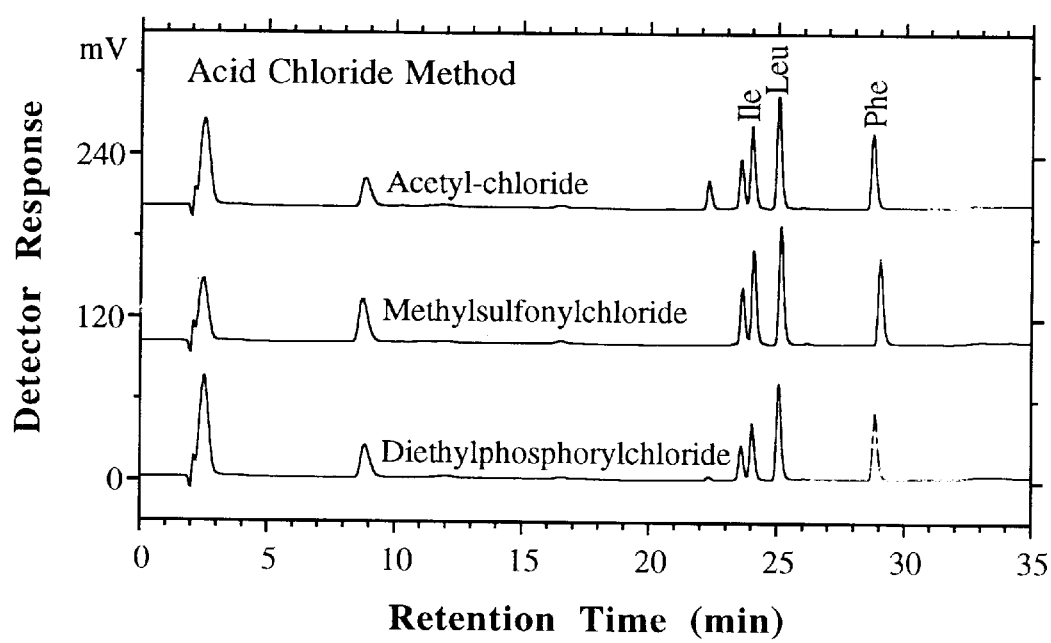
FIG. 11 demonstrates the C-terminal sequencing of a mixture of three peptides, GGI, GGL, GGF by HPLC analysis of their thiohydantoin formation using three acid chlorides and potassium thiocyanate.

In a two step process the protein is reacted with a suitable acid chloride derivative, such as acetyl chloride, methyl sulfonyl chloride, or phosphoryl chloride, under acidic conditions to yield a stable protein carboxy chloride. The protein carboxy chloride is then reacted, under acidic conditions, with either an organic salt thiocyanate, such as guanidine thiocyanate, or piperidine thiocyanate; and organic isothiocyanate, such TMS-ITC, or a metal thiocyanate, such as K+ or Na+ (iso)thiocyanate, to form a C-terminal protein thiohydantoin derivative (AA-TH). This reaction is generally described in FIG. 10 and an actual example is further shown in FIG. 11.

The protein C-terminal derivatization, as noted above, is carried out under acidic conditions, using suitable acid, such as acetic acid, trifluoroacetic acid and hydrochloric acid, under varied temperature conditions from about 20 to 80° C., preferably about 55 to 65° C. Suitably the time period for reaction is from about 5 to 80 minutes, preferably from about 30 to about 45 minutes.

Cleavage of the C-terminal TH-AAs from the protein may be carried out under either acidic or basic conditions as described above. Suitably for automated sequencing, the cleavage occurs under basic conditions. A suitable reagent for such purposes is use of the novel reagents novel reagent, a mixture a thiocyanate, preferably an alkali metal or alkaline earth metal thiocyanate, more preferably sodium or potassium thiocyanate, or an alkali metal or alkaline earth metal di-thionite ($S_2O_4$), preferably potassium or sodium di-thionite ($S_2O_4$), and a buffer, such as a Na phosphate buffer, carbonate buffer or a borate buffer, preferably a Na phosphate buffer, in an organic solvent. Preferably the reagent is a mixture of a buffer, preferably a Na phosphate buffer, and potassium or sodium thiocyanate or potassium or sodium di-thionite ($S_2O_4$) in an organic solvent, such as acetonitrile.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions rum under anhydrous conditions unless otherwise indicated.

EXAMPLE 1

Preparation of Acetylisothiocyanate Coupling Solutions

Reagents and Standards: Trimethylsilylisothiocyanate (TMS-ITC), guanidine thiocyanate (Gu.HSCN) or piperidine HSCN, acetylchloride, acetic anhydride and acetic acid (Aldrich Chemical®).

a) From Gu.SCN: 200 mg of Gu.SCN was dissolved in 0.8 mil of acetonitrile in a screw cap micro centifuge tube (1.6 ml polypropylene freeze vials from Sigma). 50 ul of acetic anhydride and 5 ul acetic acid were added and mixed. To this mixture 0.15 ml of acteylchloride was added and mixed on a Vortex mixer for about 5 minutes. Gu.HCl was precipitated and separated from the acetylisothiocyanate (Ac-NCS) solution by centrifugation.

b) From TMS-ITC: To 0.5 ml of acetonitrile, 0.3 ml of TNS-ITC, 0.15 ml of acetyl chloride, 50 ul of acetic anhydride and 5 ul of acetic acid were added and mixed. In this case there is no need to centrifuge.

Both reagents as produced in steps (a) and (b) produce a similar result.

EXAMPLE 2

Preparation of Amino Acid Thiohydantoin Standards

Using the acetylisothiocyanate reagent prepared in accordance with Example 1, steps (a) or (b) above the preparation of amino acid thiohydantoin standards is performed using readily available free amino acids purchased from commercial source, such as from Beckman Laboratories or Pierce Chemicals. Free amino acids and small peptides may also be purchased from Sigma Chemicals or Aldrich Chemicals.

a) Dry amino acids individually or in a mixture (<10 nmol ea. approx. 3 ul of the amino acid standard mixture dried in the screw cap freeze vials using an oven or Reacti-Therm heating block at 65° C.) were mixed with 50–60 ul of the acetylisothiocyanate coupling solution and sonicated for approx. 10 minutes. The vials were then heated at 65° C. for 40 minutes. After cooling the vials to room temperature, the reaction mixture was diluted with water to 0.5 ml and mixed thoroughly until the oily liquid dissolves in water (approx. 5 min). The vials were heated again at 65° C. for 45–60 minutes. An aliquot of the reaction mixture (25–50 ul) was analyzed by HPLC.

HPLC analysis: Thiohydantoins were separated using a suitable column, such as a Hypercarb pH (3.0×100 mm, graphitized carbon, Shandon from Alltech) column using 0.1% TFA in water (solvent A) and in acetonitrile (solvent B). Flow rate used was 0.4 ml/min at 35° C. (using a column heater). A linear gradient of 3 to 60% B at 30 min followed by a wash with 100% B is used for the AA-TH separations. The Trp-TH eluted in the wash. Other suitable columns may be substituted (see Bailey, et al., Protein Science, 1:1662-33 (1992)). Thiohydantoins were detected at 265 nm except for Ser-Th and Thr-Th which were detected at 319 nm for the dehydrated forms.

The Ser and Thr yield considerable amounts of dehydrated products even under these acidic conditions noted herein. Little if any problems have been seen with Asp, Pro, S-Cm-Cys and are quite easily make by this procedure. The reaction conditions, with suitable modifications recognized by one of skill in the art, may be used to prepare 10–100 mg of the A-TH standards rapidly.

For manual sequencing the sequencing yield for the first cycle is >90%, and for the second cycle is about 50% of the first cycle. Present conditions have Ser and Cys yielding the same thiohydantoin on HPLC.

EXAMPLE 3

Terminal Carboxy Sequencing of Protein or Peptides

Using the acetylisothiocyanate reagent prepared in accordance with Example 1, steps (a) or (b) above the an immobilized peptide or protein of choice is prepared for sequencing from the carboxy terminal end. In this Example the protein Lysozyme is demonstrated. Alternatively, the proteins recombinant immunoglobulin G (IgG), β-lactoglobulin, and bovine serum albumin (BSA) have been performed using the same procedure as indicated below.

The lysozyme was immobilized on a Sequelon®-DITC (Millipore Corp. Bedford, Mass.) (or equivalent) membrane in accordance with manufacturer's suggestions. The Sequelon® disk containing the lysozyme was treated with 0.1 to 0.2 ml of acetylisothiocyanate coupling solution at 45 to 75° C. for, preferably at 65° C., for 40 to 100 min, preferably for 40 min. The protein disk was washed successively with acetonitrile, methanol and 30% methanol in water (v/v). The C-terminal thiohydantoin formed was cleaved from the lysozyme using 0.15 ml of 0.1M Na phosphate pH 11 at 60° C.) or pH 12 (at ambient temperature) containing 0.1M KSCN and 30% methanol solution for 5–80 min, preferably 15 at 60° C. and 40 min at room temperature. The protein disk was removed from the cleaving solution and the thiohydantoin was acidified with dilute acetic acid. The cleaved thiohydantoin was determined by HPLC using a Hypercarb column as in Example 2 above.

For the second cycle the disk containing the protein was washed successively with 5% trifluoroacetic acid in water, 30% methanol-water and acetonitrile and the derivatization procedure described above was repeated in its entirety.

EXAMPLE 4

Carboxyl-Terminal Derivatization Using Acid Chlorides and Thiocyanates

A equimolar peptide mixture of Gly-Gly-Leu, Gly-Gly-Ile and Gly-Gly-Phe was immobilized on a Sequelon®-DITC membrane disk as in Example 3 above. The disk containing the peptide was treated first with excess of acid chlorides (e.g.:acetylchloride, methylsulfonylchloride, phosphoryl chloride and diethylphosphorylchloride etc.) at about 55–60° C., for about 10 min. The disk was washed with anhydrous acetonitrile and then treated with thiocyanate solution (e.g.:saturated solution of KSCN in acetone, guanidine thiocyanate in acetonitrile and trimethylsilyl-isothiocyanate in acetonitrile etc.), preferably about 2M guanidine thiocyanate in acetonitrile, at 22° C. to 90° C., preferably 10 min at 55–60° C. The disk was washed successively with acetonitrile, methanol and 30% methanol solution (v/v). The thiohydantoins formed were cleaved and determined by HPLC as in Example 2 and 3.

EXAMPLE 5

Preparation of Amino Acid Thiohydantoin Standards

The following method was used for preparing the amino acid thiohydantoin standards in large amounts. This procedure is a modification of the method described in Example 2 although other modifications can be made. 4×1.25 g each of guanidine thiocyanate was dissolved in 4×9 ml of acetonitrile in four separate 15 ml polypropylene screw capped tubes. To each tube 0.375 ml of acetic anhydride and 0.065 ml of acetic acid and 1.25 ml of acetylchloride were added and vigorously using a shaker (Tekmar). The resulting guanidine HCl was separated by centrifugation and the supernatant (coupling solution) was combined in a 250 ml round bottomed flask. About 500 mg of free amino acid was dissolved in the coupling solution. The reaction mixture was heated at 30° C. to 90° C., preferably at 60° C., for 20–120 min, preferably for 60 min. The reaction mixture was cooled to room temperature and diluted with equal volume of water and re-heated as above, preferably at 60° C. for 60 min. After cooling the reaction mixture was dried using a rotary evaporator. The residue was dissolved in ethyl acetate (~50–75 ml) and the soluble material was transferred to an another flask and dried as above. This residue was dissolved in minimum amount warm water and the flask was left in a refrigerator overnight. The yellowish powder was separated from the solution, washed with ether or methylene chloride and dried. Yield of the thiohydantoins was depended only on the solubility of the amino acids in the coupling solution. For proline and threonine the yields were ~90% and 40% respectively. The thiohydantoins were >98% pure by HPLC with a single peak. The elemental analysis and the absorption spectra were consistent with those of the previously published results.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A process for sequencing a peptide or protein by carboxyl terminal derivatization consisting essentially of:
   1) the sequential reaction of said peptide or protein with an acid chloride derivative to yield a protein carboxy chloride derivative, and wherein the addition of the acid chloride is carried out under acidic conditions;
   2) reacting the protein carboxy chloride derivative with an organic salt thiocyanate, an organic isothiocyanate, or an alkali or alkaline earth metal salt of an isothiocyanate, to form a carboxy-terminal thiohydantoin amino acid.

2. The process according to claim 1 wherein the acid chloride derivative is acetyl chloride, methyl sulfonyl chloride, diethyl phosphoryl chloride, or phosphoryl chloride.

3. The process according to claim 1 wherein the acidic conditions are obtained using acetic acid, trifluoroacetic acid, hydrochloric acid or mixtures thereof.

4. The process according to claim 1 wherein the protein or peptide is covalently attached to a solid support.

5. The process according to claim 1 wherein the alkali salt of an isothiocyanate is potassium or sodium isothiocyanate; the organic isothiocyanate reagent is guanidine thiocyanate, or piperidine thiocyanate; or the organic salt thiocyanate is trimethylsilyl isothiocyanate.

6. The process according to claim 5 wherein the organic thiocyanate reagent is guanidine thiocyanate, or piperidine thiocyanate.

7. The process according to claim 1 wherein the carboxy-terminal thiohydantoin amino acid is cleaved with an acid or base to release a thiohydantoin amino acid.

8. The process according to claim 7 wherein the released thiohydantoin amino acid is analyzed for determination of the amino acid.

9. The process according to claim 7 wherein the cleavage is by a mixture of buffer and an alkali metal or alkaline earth metal thiocyanate, or an alkali metal or alkaline earth metal di-thionite ($S_2O_4$).

10. The process according to claim 7 wherein the carboxy-terminal thiohydantoin amino acid cleavage is by thiocyanic acid and acetic acid.

11. The process according to claim 10 wherein the water is added to the reaction mixture.

12. The process according to claim 7 wherein the cleavage is by a mixture of buffer and potassium thiocyanate or potassium di-thionite ($S_2O_4$).

13. The process according to claim 12 wherein the molar concentration of each reagent is about 0.1M to 0.2M.

14. The process according to claim 12 wherein the reaction process is at ambient temperature.

15. The process according to claim 12 wherein the reaction process is from about 40 to 60° C.

16. The process according to claim 12 wherein the pH is from about 8 to 12.

17. The process according to claim 12 wherein the buffer is sodium phosphate, carbonate, or borate.

18. The process according to claim 12 which further comprises an organic solvent.

19. The process according to claim 18 wherein the organic solvent is acetonitrile.

* * * * *